United States Patent [19]

Marx et al.

[11] 4,130,665
[45] Dec. 19, 1978

[54] A-NORANDROSTANE DERIVATIVES

[75] Inventors: Arthur F. Marx, Delft; Cornelis Vos, Pijnacker, both of Netherlands

[73] Assignee: Gist-Brocades N.V., Netherlands

[21] Appl. No.: 891,288

[22] Filed: Mar. 28, 1978

[30] Foreign Application Priority Data

Mar. 28, 1977 [GB] United Kingdom ............... 13003/77

[51] Int. Cl.² ...................... A61K 31/12; C07C 49/46
[52] U.S. Cl. ............................. 424/331; 260/586 E
[58] Field of Search ...................... 260/586 E; 424/331

[56] References Cited

U.S. PATENT DOCUMENTS 4,075,233  2/1978  Marx et al. ....................... 260/586 E

FOREIGN PATENT DOCUMENTS 1768569  7/1977  Fed. Rep. of Germany ....... 260/586 E

OTHER PUBLICATIONS

Canceill et al., Compt. Rend. (Acad. Science, Paris), Ser. C. 285, No. 1, pp. 37–40 (1977).
Chemical Abstracts, vol. 71, 3540(c) (1969).

*Primary Examiner*—Gerald A. Schwartz
*Attorney, Agent, or Firm*—Robert E. Burns; Emmanuel J. Lobato; Bruce L. Adams

[57] ABSTRACT

Therapeutically useful A-nor-androsta-3(5),16-dien-2-one derivatives of the general formula:

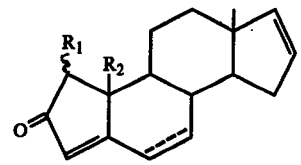

I wherein $R_1$ and $R_2$ each represent a hydrogen atom or a methyl group, process for their preparation by dehydrating in the 16–17 position a corresponding 17-hydroxy compound, and pharmaceutical compositions for the treatment of dermatological disorders, which comprise, as an active ingredient at least one of the A-nor-steroids as defined by formula I, are disclosed.

7 Claims, No Drawings

A-NORANDROSTANE DERIVATIVES

THIS INVENTION relates to therapeutically useful steroids of the androstane series, to a process for their preparation and to pharmaceutical compositions containing the steroids as active principle.

The steroids of the present invention are the A-nor-androsta-3(5),16-dien-2-one derivatives of the general formula:

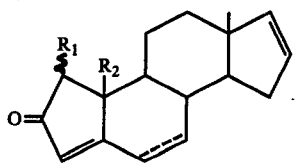

wherein $R_1$ and $R_2$ are the same or different and each represents a hydrogen atom or a methyl group, the dotted line in the 6–7 position indicates the optional presence of an additional double bond and the wavy line in the 1 position indicates that the substituent $R_1$ is either in α- or β-configuration.

The steroids of the present invention are therapeutically useful compounds; they have strong topical anti-androgenic activity, whereas the systemic anti-androgenic activity is very weak. The compounds have a very low toxicity (acute $LD_{50}$ in mice intraperitoneally: above 1000 mg/kg animal body weight) and are devoid of progesterone- and corticosteroid-like activity and anti-gonadotrophin activity.

The compounds may be used in the treatment of various dermatological disorders, including hirsutism, acne, seborrhoea, alopecia androgenetica and baldness. Of outstanding interest is the compound A-nor-androsta-3(5),16-dien-2-one.

The androstane derivatives of the above formula may be prepared by application of methods known for the preparation of analogous compounds.

According to a feature of the invention the steroids are prepared by dehydrating in the 16–17 position A-nor-testosterone derivatives of the general formula:

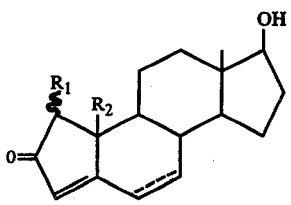

wherein $R_1$ and $R_2$ are as hereinbefore defined.

The dehydration can be carried out, for example, by reacting a compound of formula II with an alkanesulphonyl halide (e.g. mesyl chloride) to form a corresponding 17-alkane-sulphonyloxy derivative. The reaction is preferably carried out in an inert organic medium, such as pyridine.

The resulting 17-alkanesulphonyloxy derivative can then be converted by heating in a suitable organic solvent, such as dimethylformamide, in the presence of lithium chloride into a A-nor-androsta-3(5),16-dien-2-one derivative of formula I.

The compounds of general formula II, A-nor-testosterone derivatives, are known compounds.

The following non-limitative Examples illustrate the preparation of the steroids of the present invention.

EXAMPLE I (a) To a stirred solution of 1 g of A-nor-testosterone in 6 ml of dry pyridine, cooled by means of an ice-bath to −5° C., 12 ml of methanesulphonyl chloride (mesyl chloride) were added at such a rate that the temperature of the reaction mixture was kept below 0° C. After completion of the addition the ice bath was removed and the temperature of the reaction mixture was allowed to rise to room temperature. After completion of the reaction the mixture was poured into 70 ml of water, the precipitate collected, washed well with water and dried in vacuo. The crude A-nor-testosterone 17-mesylate (1.2 g) so obtained was not further purified, but used as such in the next stage.

(b) A solution of 1.2 g of A-nor-testosterone 17-mesylate (obtained as described above) and 1.4 g of lithium chloride in 14 ml of dimethylformamide was heated with stirring to 130° C. under nitrogen. After 75 minutes the mixture was cooled to about 50° C. and then poured into 150 ml of water. The oily precipitate was dissolved in methyl isobutyl ketone and the organic solution concentrated to dryness under reduced pressure. The residue was dissolved in toluene and chromatographed on silica gel impregnated with silver nitrate (100 g of $SiO_2$ containing 12% $AgNO_3$; elution with toluene +2% acetone). The fractions containing the product were combined, washed with 25% ammonia and water. The solution was then concentrated to dryness in vacuo and the residue crystallized from methanol/water. The yield was 0.12 g of pure A-nor-androsta-3(5),16-dien-2-one, m.p. 75°–76° C. mol. peak in mass spectrum (m/e): 256.

EXAMPLE II

Following the procedures described in Example I(a) and (b), 1 g of A-nor-6-dehydro-testosterone was converted via the corresponding 17-mesylate into 0.11 g of A-nor-androsta-3(5),6,16-trien-2-one, m.p. 156°–158° C. mol. peak in mass spectrum (m/e): 254.

EXAMPLE III

Following the procedures described in Example I(a) and (b), 0.8 g of 4,19-bisnor-17β-hydroxy-androst-3(5)-en-2-one were converted via the corresponding 17-mesylate into 0.09 g of 4,19-bisnor-androsta-3(5),16-dien-2-one, m.p. 80°–84° C. mol. peak in mass spectrum (m/e): 242.

EXAMPLE IV

Following the procedures described in Example I(a) and (b), 0.9 g of 1-methyl-A-nor-testosterone were converted via the corresponding 17-mesylate into 0.1 g of 1-methyl-A-nor-androsta-3(5),16-dien-2-one, m.p. 89.5°–92° C. mol. peak in mass spectrum (m/e): 270.

The A-nor-androsta-3(5),16-dien-2-one derivatives of general formula I may be used as anti-androgenic agents in humans and animals. The daily dose and preferred concentration vary depending on the route of administration. For therapeutic purposes the compounds may be employed in the form of pharmaceutical preparations customarily employed for administration of therapeutically active substances. The invention therefore provides pharmaceutical compositions comprising, as the active ingredient, an A-nor-androsta-3(5),16-dien-2-one derivative of formula I in association with a pharmaceutically acceptable carrier. Pharmaceutical compositions in which the active ingredient is selected from A-nor-androsta-3(5),16-dien-2-one, A-nor-androsta-3(5),6,16,trien-2-one, 4,19-bisnor-androsta-3(5),16-dien-2-one and 1-methyl-A-nor-androsta-3(5),16-dien-2-one are particularly preferred.

The compounds of formula I are preferably administered topically. Preferred pharmaceutical compositions are accordingly those suitable for topical use such as gels, lotions, creams, ointments, sticks and emulsions. The preferred concentration of the active ingredient in compositions for topical administration is 0.01 to 10% by weight.

The active substances may also be made up in a form suitable for subcutaneous administration, i.e. as a solution or as a suspension or emulsion in an organic liquid usually employed for injectable preparations, for example a vegetable oil such as olive oil. Compositions for subcutaneous administration such as solutions or suspensions preferably contain from 5 to 250 mg/ml and the preferred daily dosage is from 1 to 5 ml.

Veterinary compositions for subcutaneous administration preferably contain 1 to 100 mg/ml and the preferred daily dosage is from 1 to 10 ml.

The following Examples illustrate the preparation of pharmaceutical compositions according to the present invention.

EXAMPLE V

A gel was prepared from the following ingredients:

| | |
|---|---|
| A-nor-androsta-3(5),16-dien-2-one | 2 g |
| ethyl alcohol | 70 g |
| propylene glycol | 8 g |
| Carbopol 940 | 1 g |
| diisopropanolamine | g |
| water | q.s.p.100 ml |

EXAMPLE VI

A lotion was prepared from the following ingredients:

| | |
|---|---|
| A-nor-androsta-3(5),6,16-trien-2-one | 2 g |
| ethyl alcohol | 49 g |
| polyethylene glycol | 49 g |

EXAMPLE VII

A stick for local application was prepared from the following ingredients:

| | |
|---|---|
| A-nor-androsta-3(5),16-dien-2-one | 2 g |
| ethyl alcohol | 80 g |
| perfume oil | 1.4 g |
| sodium stearate | 6 g |
| glycerol | 2.6 g |
| propylene glycol | 3 g |
| water | 5 g |

EXAMPLE VIII

A cream for local application was prepared from the following ingredients:

| | |
|---|---|
| 4,19-bisnor-androsta-3(5),16-dien-2-one | 0.5 g |
| ceto stearyl alcohol | 7.2 g |
| polyoxyethylene cetyl ether | 1.8 g |
| liquid paraffin | 6 g |
| vaseline | 15 g |
| methyl paraben | 0.2 g |
| water | q.s.p. 100 g |

We claim:

1. A-nor-androsta-3(5),16-dien-2-one derivatives of the formula:

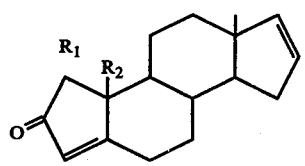

I wherein $R_1$ and $R_2$ are the same or different and each represents a hydrogen atom or a methyl group, the dotted line in the 6-7 position indicates the optional presence of an additional double bond and the wavy line in the 1 position indicates that the substituent $R_1$ is either in $\alpha$- or $\beta$-configuration.

2. A-nor-androsta-3(5),16-dien-2-one.
3. A-nor-androsta-3(5),6,16-trien-2-one.
4. 4,19-Bisnor-androsta-3(5),16-dien-2-one.
5. 1-Methyl-A-nor-androsta-3(5),16-dien-2-one.
6. A pharmaceutical composition for the treatment of dermatological disorders which comprises, a dermatologically effective amount of an active ingredient comprising an active ingredient at least one of the A-nor-androsta-3(5),16-dien-2-one derivatives as claimed in claim 1 in admixture with a pharmaceutically acceptable carrier.
7. A pharmaceutical composition according to claim 6 in which the active ingredient is selected from the group consisting of A-nor-androsta-3(5),16-dien-2-one, A-nor-androsta-3(5),6,16-trien-2-one, 4,19-bisnor-androsta-3(5),16-dien-2-one and 1-methyl-A-nor-androsta-3(5),16-dien-2-one.